United States Patent [19]

Chiesi et al.

[11] Patent Number: 5,049,566

[45] Date of Patent: Sep. 17, 1991

[54] IMIDAZOLE [4,5-C] PYRIDINE DERIVATIVES HAVING GASTRIC ACID ANTISECRETORY ACTIVITY AND PHARMACEUTICAL COMPOSITIONS CONTAINING THEM

[75] Inventors: Paolo Chiesi; Vittorino Servadio; Roberta Rassetti, all of Parma, Italy

[73] Assignee: Chiesi Farmaceutic S.p.A., Parma, Italy

[21] Appl. No.: 493,957

[22] Filed: Mar. 14, 1990

Related U.S. Application Data

[63] Continuation-in-part of Ser. No. 223,610, Jul. 22, 1988, abandoned.

[30] Foreign Application Priority Data

Jul. 31, 1987 [IT] Italy ............................... 21538 A/87

[51] Int. Cl.$^5$ ................... A61K 31/435; C07D 471/04
[52] U.S. Cl. ...................................... 514/303; 546/118
[58] Field of Search ......................... 546/118; 514/303

[56] References Cited

FOREIGN PATENT DOCUMENTS 213474 3/1987 European Pat. Off. ............ 548/329
301422 2/1989 European Pat. Off. .

Primary Examiner—Bernard Dentz
Attorney, Agent, or Firm—Walter H. Schneider

[57] ABSTRACT

Imidazo[4,5-c] pyridine compounds and physiologically acceptable salts thereof having antiulcer and gastric acid antisecretory activities and pharmaceutical compositions containing them.

3 Claims, No Drawings

IMIDAZOLE [4,5-C] PYRIDINE DERIVATIVES HAVING GASTRIC ACID ANTISECRETORY ACTIVITY AND PHARMACEUTICAL COMPOSITIONS CONTAINING THEM

This is continuation in part of application Ser. No. 223,160 filed July 22, 1988 now abandoned.

The present invention relates to imidazo[4,5-c]pyridine compounds and to physiologically acceptable salts thereof, having antiulcer and gastric acid antisecretory activities, to a process for the preparation thereof and to pharmaceutical compositions containing them.

The compounds of the invention have the following general formula:

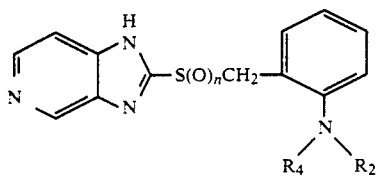

wherein $R_1$ and $R_2$, which can be the same or different, are each H or $C_1$-$C_4$ alkyl; n is 0 or 1.

A remarkable percentage (5-20%) of the world population is afflicted, at some point of its existence, with gastroduodenal ulcer.

The illness 'medical treatment, principally based till now on reduction or neutralization of the intraduodenal and intragastric acidity, has marked considerable progress in the last 10 years.

The arrival of the antagonists of $H_2$ mine receptors, cimetidine and ranitidine, has caused a true revolution in this therapeutic sector, thus stimulating the research for new drugs of increased power and effectiveness.

As a result, a new pharmacological class of antisecretory drugs has been located, the so-called inhibitors of the protonic pump, the more representative being omeprazole, a substituted derivative of benzimidazole endowed with a lasting and powerful inhibiting activity of gastric acid secretion. The search for drugs of an ever increasing power of inhibition of the acid secretion has however created problems. In fact, deep and prolonged inhibition of the acid secretion can cause morphologic alterations in the mucous membrane.

A high incidence of carcinomas at the bottom of the stomach has been observed in animals treated over a long period with either omeprazole or powerful antagonists of $H_2$ receptors, so much so that development of some of these products has been temporarily or definitively shelved.

Moreover, among the patients treated with very powerful anti-secretory agents, a considerable relapse frequency, direct consequence of the type of therapy, has been noted.

Novel therapeutic prospects in the treatment of gastroduodenal ulcer were opened recently by cytoprotective drugs which seem to act by strengthening the defense of the mucous barrier, by means of a process independent from the inhibition of acid secretion.

The mucous membrane's protective drugs have rekindled the interest in the study of the ulcerative mechanism giving new credit to the hypothesis that it derives from a diminished resistance to the acid-peptic activity rather than to an increase of the secretory activity.

The problem of therapy of ulcer therefore remains unresolved. A rational approach seems to be control of acid secretion rather than a too strong inhibition, on one side, and improved resistance of the mucous membrane to the attacks of the acid and of the other damaging agents, on the other.

Future strategy in the therapy of peptic ulcer can lie therefore with the use of inhibitors of acid secretion combining a protective action of the mucous membrane.

In this perspective, various classes of molecules have been prepared in the aim to increase their potentiality of use in the treatment of gastroduodenal ulcer.

As previously said, considerable interest was caused recently by a new class of inhibitors of gastric acidity consisting in benzimidazole derivatives, of which the omeprazole seems to be at this moment the more powerful.

Omeprazole, described in European Patent No. 5129, can be considered the final result of a series of studies on analogous structures object of previous patents Nos. DE 2504252 and DE 2548340.

Heterocyclic thioalkyl and thiosulfinyl derivatives of various structures, having antisecretory activity, are also disclosed in EP-A-74.341, GB Patent No. 2.134.523, GB Patent No. 2.038.825, GB Patent No. 2.161.160, BE Patent n. 903128 and in EP-A-201.094. More recently imidazopyridine derivatives have been disclosed in EP 187977 and in EP 234690. Nevertheless said compounds, on the basis of the activity results reported in the above-mentioned patents, seem to show no remarkable advantages in comparison with omeprazole. Some new compounds belonging to the class of imidazo[4,5 c]pyridine which resulted to be very active in inhibiting acid secretion have now been synthesized.

The aminophenyl-methylthio (or sulfinyl) imidazo[4,5 c]pyridines object of the invention can so represent the parent compounds of a new class of acid secretion inhibitors, showing also activity in preventing gastric lesions.

The process for the preparation of derivatives of formula (I) in which n=0 consists in reacting a compound of formula:

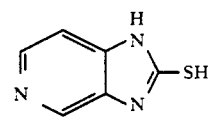

with a compound of formula:

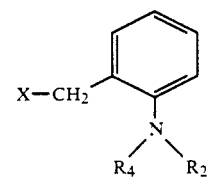

wherein X is a leaving group, preferably an halogen atom.

The reaction is conveniently carried out in the presence of a solvent or a mixture of solvents which are inert under the reaction conditions, generally in the presence of a base. Suitable bases are, in particular, inorganic bases, such as sodium or potassium hydroxides, or organic bases, such as triethylamine or tertiary amines.

Particularly suitable solvents or solvent mixtures are alcohols, such as methanol or ethanol, mixtures of alcohols and water, preferably ethanol water; ethers, such as tetrahydrofuran or dioxane; halogenated hydrocarbons, such as methylene chloride or chloroform; amides, such as formamide or dimethylformamide.

The reaction temperature usually ranges from room temperature to the boiling temperature of the reaction mixture.

A particularly convenient preparation method consists in transforming a compound of formula (II) into the corresponding alkali salt using, for example, a sodium hydroxide solution, subsequently adding to the solution a compound (III), in which X preferably represents a halogen such as chlorine, bromine or iodine. Corresponding compounds of formula (I) in which n is 1 are obtained by subsequent oxidation of the sulfur atom to sulfinyl group (S→0).

The used oxidation agents are those generally employed in the trasformation of S into S—0, which are selected from: peracids, particularly 3 chloroperbenzoic acid, 4-nitroperbenzoic acid; hydrogen peroxide, peresters, sodium metaperiodate, selenium dioxide, manganese dioxide, etc.

Oxidation is conveniently carried out in an organic solvent inert in the reaction conditions, such as ethanol, dimethylformamide, ethyl ether, a halogenated hydrocarbon, preferably methylene chloride, chloroform, dichloroethane, or an aromatic hydrocarbon, such as benzene and similar.

The oxidation agent is generally used in excess to the compound to be oxidized. Oxidation is conveniently effected at room temperature or at a lower temperature from $-10°$ C. to $0°$ C.

Compounds of general formula I can be transformed into the pharmaceutically acceptable salts, by addition of therapeutically compatible organic or inorganic acids or bases. Suitable acids may be: hydrochloric, hydrobromic, phosphoric, sulfuric, citric, acetic, succinic, maleic, methanesulfonic, 4-toluenesulfonic acids, and the like. Particularly convenient bases are alkaline hydroxides, such as sodium or potassium hydroxide.

Compounds of formula (I) in which $n=1$, can be in form of optical isomers or racemates, all these forms being comprised in the present invention.

Reaction intermediates of formula (II) and (III) are generally commercially available or they can be prepared according to procedures known in literature.

The invention is described in more detail in the following non-limiting examples.

EXAMPLE 1

2-[2-(N,N-dimethylanilyl)methylthio]imidazo[4,5-c]pyridine (IV)

50 g (0.33 mole) of 2-mercaptoimidazo[4,5-c]pyridine were dissolved in 785 ml of a solution of 25,64 g (0,63 mole) of sodium hydroxide in a 16:1 ethanol/water mixture. Then 64.76 g (0.31 mole) of 2-chloromethyl-N,N-dimethylaniline hydrochloride were added and the mixture was reacted for 2 hours at room temperature; thereafter it was cooled to about 5°-8° C. and filtered.

The resulting solid was washed with water, 4:1 diethylether:ethylacetate mixture and the product was crystallized from 1-methylpropanol to give 61 g of product (0.21 mole).

Yeld ;65%; C15H16N4S; M.W. 284.39; m.p. 183°-186° C.

EXAMPLE 2

2-[2-N,N-dimethylanilyl)methylsulfinyl]imidazo[4.5-c]pyridine (V)

50 g (0.176 mole) of the thioether prepared according to example 1 was dissolved in 1300 ml of a 1:5:10 of ethanol/chloroform/dichloromethane mixture. 56.72 g (0.179 mole) of 55% 3-chloroperbenzoic acid was added to the starting solution in anhydrous medium, at a temperature of $\leq 0°$ C., under strong stirring and the mixture was left to react in the cool for 1 hour, then it was warmed to room temperature and filtered. The solid is washed with aqueous sodium hydroxide, chloroform, diethylether, ethanol, taken up in 1:4 chloroform/diethylether mixture, and then washed with diethylether and dried under reduced pressure at 35° C. 32 g (0.106 mole) of product were obtained.

Yield 61%; C15H16N4OS; M.W. 300.39; m.p. 196°-198° C.

EXAMPLE 3

2-2[N,N-dimethylanilyl)methylsulfinyl]imidazo[4,5-c]pyridine potassium salt (VI)

14 g (0.046 mole) of the compound prepared according to example 2 were suspended in 200 ml of ethanol.

3 g (0.046 mole) of potassium hydroxide dissolved in 10 ml of water were added to the mixture under stirring until complete dissolution.

The mixture was dried at 40° C. under reduced pressure and the residue was washed with ethanol and chloroform.

The solid was removed by filtration and the solution dried. The residue was taken up in 165 ml of 10 ethanol-diethylether mixture and dried at 40° C. under reduced pressure to yield 14 g of product.

Yield 90%; ; C15H15KN4OS; M.W. 338.48; m.p. 244°-246° C.

The compounds of the invention have been subjected to a pharmacological study as hereinafter reported, using as reference compounds cimetidine and omeprazole, parent compound of the new antisecretory compounds class of the proton pump inhibitors.

Antisecretory activity - Shay ulcers

The gastric secretory inhibitory activity of the compounds of general formula (I) was determined in case of hypersecretion induced in the rat by ligation of gastroduodenal junction according to the procedure described by Shay (Shay H. et al, Gastroenterology 5, 43-61, 1945).

Male CD (Charles River) rats, of body weight higher than 180 g, were fed with a standard diet and housed under constant temperature and relative humidity conditions at least for 5 days before the test. Thereafter, they were fasted for 24 hours, with water ad libitum, which period was sufficient to assure a good gastric emptying, then laparectomized under light ether anesthesia, so as to allow to effect a pylorus ligation as closer as possible to the gastroduodenal junction. Two hours after the ligation, the animals were killed by means of an ether excess and stomaches were removed. Gastric contents were recovered, after filtration through a gauze, and placed in graduated test-tubes and centrifuged at $3000 \times g$ for 15 minutes. The following parameters were evaluated on the surnatant: volume (ml); pH; free acidity by conversion of pH into $H^+$ /uEq by means of Moore table (Ann. New York Acad. Sci. 1967, 866-874); titrable acidity, by titration of an amount with 0.02N NaOH, using phenolphtalein as the indicator.

Both free and titrable acid concentrations were then multiplied by the respective secretion volume, to obtain hydrochloric acid output secreted during the 2 hours ligation.

Compounds under test were administered either by the intraduodenal route, suspended in 0.5% Methocel in a 5 ml/kg volume, immediately after pylorus ligation, or by the intravenous route (1 ml/kg) dissolved in 0.5 M methanesulfonic acid, at the moment in which ligation was performed. Control animals were administered with the only solvent, in an amount of 5 ml/kg and 1 ml/kg respectively by the intraduodenal or intravenous routes.

The results were expressed as percent inhibition of hypersecretion induced by pylorus ligation in the control rats.

The obtained results are reported in table 1 as:
— $ED_{50}$(μmole/kg) calculated on the basis of the equation of the linear tract of dose-effect curves obtained with the test compounds on volume, free and titrable acidities;

approximate value of intrinsic activity and PR potency ration in comparison with Omeprazole, calculated as ratio of mean $ED_{50}$, on the 3 parameters of the test compound to mean $ED_{50}$ of the control compound.

TABLE 1

Inhibitory effect of compounds of general formula (I) for the secretion of hydrochloric acid in the stomach (Shay ulcers) in comparison with omeprazole and cimetidine.

| Compounds | | $ED_{50}$ (μmoli/kg) | | | | |
|---|---|---|---|---|---|---|
| | | volume | free acid output | titratable acid output | α | PR |
| Omeprazole | i.d. | 4.2 | 1.8 | 2.3 | 1 | 1 |
| | i.v. | 5.7 | 1.6 | 2.1 | 1 | 1 |
| Cimetidine | i.d. | 33.9 | 28.7 | 23.4 | 1 | 5 |
| | i.v. | 47.3 | 24.1 | 23.9 | 1 | 11.5 |
| IV CHF 1754 | i.d. | 19.7 | 5.5 | 6.9 | 1 | 3.8 |
| | i.v. | 15.0 | 4.5 | 4.0 | 1 | 2.5 |
| V CHF 1781 | i.d. | *— | — | — | — | — |
| | i.v. | 76.8 | 40 | 47.1 | 0.6–0.8 | 17.2 |
| VI CHF 1842 | i.d. | 37 | 21 | 23.6 | 1 | 9.7 |
| | i.v. | 50.96 | 49.15 | 49.1 | 1 | 15.7 |

*not determined because not soluble

Lumen-perfused rat stomach in situ

The experiments were done according to Ghosh M.N. and Schild H.O. (Br. J. Pharmacol. 13, 54–61, 1958).

Charles River, CD male rats having a body weight of 280–320 g, deprived of food with free access to water for 24 hours prior to the experiment, were anesthetized with urethane 25% (1.25 g/kg/5 ml i.m.) and tracheotomized. After a midline abdominal incision, a PVC tube was inserted into the stomach via the esophagus and the stomach was perfused with saline (37° C.) at a rate of 1 ml/min. A second tube draining the pylorus was inserted through the abdominal wall for collection of gastric secretion. Acid secretion was determined at 10 minutes intervals by titration of the perfusate with 0.01 N NaOH to pH 7.0 using an autotitrator (Radiometer).

After equilibration of basal secretion an hypersecretion was induced by infusion of histamine 35 mcg/kg/min, through the femoral vein.

After reaching of the plateau of the hypersecretive response (60–70' later) the test substances were administered into the duodenum suspended in Methocel in a volume of 5 ml/kg.

Mean gastric output was determined for a 3 hours test period following drug administration. The last 30 minutes interval prior to dosing was used as a control.

The dose-response relationship was established using the maximum inhibition obtained at each individual dose.

TABLE 2

Inhibitory effect of CHF 1754 for the secretion of hydrochloric acid in the stomach. Comparison is made also with another compound of the prior art NC 1300 or 2-[(2-dimethylaminobenzyl) sulfinyl] benzimidazole, corresponding to the Compound 3 of the Belgian Patent 903128

Lumen-perfused rat stomach in situ.

| Compounds | $ED_{50}$ (μmole/kg) | |
|---|---|---|
| | free acid output | titratable acid output |
| OMEPRAZOLE | 2.23 | 2.30 |
| CIMETIDINE | 11.85 | 11.09 |
| NC 1300 | 6.1 | 4.3 |
| CHF 1754 | 2.5 | 1.8 |

Protection against gastric lesions induced in rats by necrotizing agents

The experiments were done on male rats weighing 260–300 g starved (with free access to water) for 18 hours.

Absolute ethanol was administered by gavage in the volume of 1 ml.

Test substances or the vehicle alone for the controls were given by gavage 30 minutes before the necrotizing agent in a 5% suspension of methylcellulose volume 2.5 ml $kg^{-1}$. One hour after administration of the necrotizing agent, the animals were killed and examined for lesions of the glandular portion of the gastric mucosa. The lesions presenting as blackish lesions grouped in patches of varying size, usually parallel to the major axis of the stomach, were scored according to the following arbitrary scale:

0 = normal mucosa;
1 = hyperemic mucosa, or up to 3 small patches;
2 = from 4 to 10 small patches;
3 = more than 10 small or up to 3 medium-sized patches;
4 = from 4 to 6 medium-sized paches;
5 = more than 6 medium-sized or up to 3 large patches;
6 = from 4 to 6 large patches;
7 = from 7 to 10 large patches;
8 = more than 10 large patches or extensive necrotic zones.

"Small" was defined as up to 2 mm across (max diameter), "medium-sized" as between 2 and 4 mm across and "large" as more than 4 mm across.

Animals with gastric lesion score <2 were considered protected.

$ED_{50}$ values were calculated according to Wilcoxon method.

The results are expressed in table 3

TABLE 3

Protection against gastric hemorrhagic lesions induced by absolute ethanol.

| Compounds | $ED_{50}$ (mg/kg) |
|---|---|
| OMEPRAZOLE | 73 |
| IV CHF 1754 | 23 |
| V CHF 1781 | 40 |

TABLE 3-continued

| Protection against gastric hemorrhagic lesions induced by absolute ethanol. | |
| --- | --- |
| Compounds | $ED_{50}$ (mg/kg) |
| VI CHF 1842 | 47 |

A further object of the present invention is provided by the use of compounds of general formula (I) in therapy, in the prophylaxis or inhibition of gastric acid secretion.

Compounds of general formula (I) or the pharmaceutically acceptable salts thereof can be used in the treatment of gastrointestinal diseases associated with acid hypersecretion, such as duodenal ulcer, gastric ulcer, peptic ulcer, esophagitis, Zollinger-Ellison syndrome, bleeding due to ulcer or to erosions of mucosa in gastrointestinal superior tract, relapsing ulcers, postoperatory ulcers.

Moreover, said compounds can be used for the treatment of all those conditions in which a reduction in stomach acid secretion and/or a cytoprotective action are required, such as hypersecretory gastritis and duodenitis, gastritis or dyspepsias associated with the administration of non-steroidal antiinflammatory drugs, in the prophylaxis of gastrointestinal bleedings in stress ulcers and similar conditions.

For therapeutical applications, the compounds of general formula (I) can be formulated in usual pharmaceutical compositions, which provide another object of the invention.

Pharmaceutical compositions containing as the active ingredient one compound of the invention, possibly in combination with pharmaceutically acceptable excipients, can be administered by oral, rectal, parenteral, transdermic, inhalatory or buccal routes, in any administration form.

The amount of the active ingredient is generally 0.1 to 95% by weight on the composition; in solid preparations it is generally 1 to 50% by weight of the composition; in liquid preparations 0.2 to 20% by weight and in parenteral preparations 0.1 to 10% by weight.

Solid compositions for oral administration can be in form of powder, granulates, tablets, capsules or similar forms. In said compositions the active ingredient can be in combination with a powdered solid diluent, such as calcium phosphate, lactose, saccharose, sorbitol, mannitol; potato, cereal or mais starches, dextrine, amylopectin, a cellulose derivative or gelatin, and can also contain a lubricant, such as talcum, magnesium or calcium stearate, polyethylene glycol or silica. Tablets can variously be coated according to well known methods. Hard-gelatin capsules can contain granulates of the active ingredient, together with solid powdered excipients such as lactose, saccharose, sorbitol, mannitol, starches (of the above mentioned type), cellulose derivatives or gelatin, and can also contain stearic acid or magnesium stearate or talc. Soft gelatin capsules can contain the active ingredient in admixture with an appropriate carrier, such as a vegetal oil, PEG, tensides.

Powders and granules can be microincapsulated to obtain a sustained release of the active ingredient. Tablets can be coated by a gastro-resistant coating such as wax, anionic polymers such as cellulose acetate phthalate, hydroxypropylmethylcellulose, partially methyl esterified polymers of methacrylic acid and the like, optionally in combination with a plasticizer. Such a type of formulation is particularly suited for compounds of general formula (I) in which n = 1, since said compounds can undergo degradation in acidic medium.

Other stabilization techniques known to those skilled in the art can be applied to the pharmaceutical compounds of the invention: among these, for example, complexation with cyclodextrines.

Liquid compositions for oral administration comprise solutions, suspensions or emulsions of the active ingredient, or of pharmaceutically acceptable salts thereof, in liquid diluents such as distilled water, ethanol, glycerol, non aqueous solvents such as propylene glycol or mixtures thereof.

Injectable formulations for parenteral administration can contain as excipients a pharmaceutically acceptable sterile liquid such as water or a polyvinylpyrrolidone aqueous solution, as well as an oil, such as peanut oil and possibly a stabilizer and/or a buffer. The active ingredient can be dissolved or suspended in the liquid and suitably sterilized or it can be lyophilized, in which case vials containing sterile liquid for injections to prepare the solution before use will be added to the package.

Compositions for rectal administration can be in form of suppositories in which the active ingredient is mixed with a neutral fatty base or with other binding agents or lubricants, such as polymer glycols, gelatins or others, or they can be in form of rectal gelatin capsules, in which the active ingredient is mixed with an appropriate carrier. Other formulations for rectal administration are microenemas ready to use or to restore at the moment of use.

Topical formulations can be of the conventional type, such as ointments, creams, gels, in form of transdermic systems consisting of adhesive matrices which can be applied to cutis, containing appropriate concentrations of the active ingredient which is gradually released through cutis thus entering hematic circulation.

Inhalatory compositions can be solutions, suspensions, emulsions or powders of the active ingredient to be administered through an aerosol, or to be conditioned in aerosol bombs, using a conventional propeller such as dichlorodifluoromethane, trichlorofluoromethane, dichlorotetrafluoroethane or others.

The present invention also provides sustained released compositions prepared according to conventional techniques.

The daily dosage in man of an active ingredient selected from one of the compounds of general formula (I) can range from 1 to 500 mg, preferably from 10 to 300 mg, depending on the type of treatment as well as on the used composition.

The compounds of the invention can also be combined with other medicaments, such as antacid, non-steroidal antiinflammatories and other antiulcer and/or cytoprotective drugs, such as anticholinergics, antihystaminic anti $H_2$ and prostaglandins.

We claim:

1. 2-[2-(N,N-dimethylanilyl)methylthio]imidazo[4,5-c]pyridine and pharmaceutically acceptable salts thereof.

2. A pharmaceutical composition having gastric acid antisecretory activity which comprises as the main active ingredient a compound according to claim 1 in combination with a pharmaceutically acceptable carrier.

3. A method of therapeutically treating a subject suffering from gastric acidity which comprises administering to said subject an effective amount of a composition according to claim 2.

* * * * *

UNITED STATES PATENT AND TRADEMARK OFFICE
CERTIFICATE OF CORRECTION

PATENT NO. : 5,049,566
DATED : September 17, 1991
INVENTOR(S) : Paolo Chiesi; Vittorino Servadio; Roberta Razzetti It is certified that error appears in the above-identified patent and that said Letters Patent is hereby corrected as shown below:

ON THE TITLE PAGE:

Item [75], the name "Roberta Rassetti" should read ---Roberta Razzetti---.

Item [73], the name "Chiesi Farmaceutic S.p.A." should read ---Chiesi Farmaceutici S.p.A.---.

Item [63], the number "223,610" should read ---223,160---.

Signed and Sealed this

Twenty-seventh Day of April, 1993

Attest:

MICHAEL K. KIRK

Attesting Officer

Acting Commissioner of Patents and Trademarks